(12) United States Patent
Sowa et al.

(10) Patent No.: US 9,950,276 B2
(45) Date of Patent: *Apr. 24, 2018

(54) POLYOL-INDUCED EXTRACTION OF WATER FROM ORGANIC LIQUIDS

(71) Applicant: Seton Hall University, South Orange, NJ (US)

(72) Inventors: John R. Sowa, Flossmoor, IL (US); Wyatt R. Murphy, Jr., Madison, NJ (US); Mithilesh Desphande, Springfield, NJ (US)

(73) Assignee: Seton Hall University, South Orange, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/387,946

(22) Filed: Dec. 22, 2016

(65) Prior Publication Data

US 2017/0095754 A1  Apr. 6, 2017

Related U.S. Application Data

(63) Continuation of application No. 14/209,228, filed on Mar. 13, 2014, now Pat. No. 9,545,583.

(Continued)

(51) Int. Cl.
*B01D 11/04* (2006.01)
*C02F 1/26* (2006.01)
(Continued)

(52) U.S. Cl.
CPC ............ *B01D 11/0492* (2013.01); *C02F 1/26* (2013.01); *C07B 63/00* (2013.01); *C07C 7/10* (2013.01); *C07C 17/38* (2013.01); *C07C 29/86* (2013.01); *C07C 45/80* (2013.01); *C07C 253/34* (2013.01); *C07D 207/263* (2013.01); *C07D 213/16* (2013.01); *C07D 307/06* (2013.01); *C10G 21/16* (2013.01); *C10G 33/00* (2013.01); *C10G 33/04* (2013.01); *C02F 2101/30* (2013.01); *C07C 2601/14* (2017.05)

(58) Field of Classification Search
CPC ....... B01D 11/04; B01D 11/0492; C02F 1/26; C02F 2101/13; C02F 2101/32; C02F 2101/34; C02F 2101/36; C02F 2101/38
See application file for complete search history.

(56) References Cited

U.S. PATENT DOCUMENTS

| 2,479,041 | A | * | 8/1949 | Elgin | ............... B01D 11/0488 568/869 |
| 3,234,125 | A | | 2/1966 | Bloch | |

(Continued)

FOREIGN PATENT DOCUMENTS

WO  2011155829 A1  12/2011

OTHER PUBLICATIONS

Bajpayee et al. "Concentration of Glycerol in Aqueous Microdroplets by Selective Removal of Water." Anal. Chem. 82(2010):1288-1291.

(Continued)

*Primary Examiner* — Katherine Zalasky
(74) *Attorney, Agent, or Firm* — Burns & Levinson LLP; Shawn P. Foley (57) ABSTRACT

Disclosed are methods of extracting water from a composition of an organic liquid and water, using a polyol which causes a phase separation.

23 Claims, 7 Drawing Sheets

Related U.S. Application Data (60) Provisional application No. 61/783,598, filed on Mar. 14, 2013.

(51) Int. Cl.

| | |
|---|---|
| *C10G 33/00* | (2006.01) |
| *C07C 7/10* | (2006.01) |
| *C07C 253/34* | (2006.01) |
| *C07C 17/38* | (2006.01) |
| *C07C 29/86* | (2006.01) |
| *C07C 45/80* | (2006.01) |
| *C07B 63/00* | (2006.01) |
| *C10G 21/16* | (2006.01) |
| *C07D 207/263* | (2006.01) |
| *C07D 213/16* | (2006.01) |
| *C07D 307/06* | (2006.01) |
| *C10G 33/04* | (2006.01) |
| *C10G 21/06* | (2006.01) |
| *C02F 101/30* | (2006.01) |

(56) References Cited

U.S. PATENT DOCUMENTS

| 4,379,028 A | 4/1983 | Berg et al. |
|---|---|---|
| 2003/0017132 A1 | 1/2003 | Li |
| 2009/0090894 A1 | 4/2009 | Wang et al. |
| 2011/0108481 A1 | 5/2011 | Bajpayee et al. |
| 2013/0149322 A1 | 6/2013 | von Spronsen |

OTHER PUBLICATIONS

Dhamole et al. Process Biochem. 45(2010):1672-1676.
Esquijarose et al. Separation Purif. Technol. 52(2006):95-101.
Freire et al. "Aqueous biphasic systems composed of water-stable ionic liquid + carbohydrates and their application." Green Chem. 13(2011):1536-1545.
Gu et al. "Glycerol as a sustainable solvent for green chemistry." Green Chem. 12(2010):1127-1138.
McConvey et al. Org. Proc. Res. Dev. 16(2012):612-624.
Renard. J. Chem. Eng. Data. 11(1966):169-171.
Renard et al. J. Chem. Eng. Data. 10(1965):152-155.
Renard et al. J. Chem. Eng. Data. 12(1967):33-36.
Renard et al. J. Chem. Eng. Data. 13(1968):485-488.
Takamuku et al. J. Phys. Chem. 105(2001):6236-6245.
Wang et al. Chem. Eng. Sci. 63(2008):2595-2600.
Wolfson et al. Environ. Chem. Lett. 5(2007):67-71.
Yesong et al. Enzyme Micobiol. Technol. 35(2004):592-597.
Water Purified With Oil, Scientific American, Dec. 2012, p. 38 (article by avid Bell about Anurag Bajpayee).

* cited by examiner

— KEROCENE- FRESH
—*— KEROCENE- WATER SAT
—□— KEROCENE AFTER Gly TREATMENT

FIG. 7B

—+— WATER SAT WITH KEROCENE
—◆— KEROCENE WATER AFTER Gly TREATMENT

POLYOL-INDUCED EXTRACTION OF WATER FROM ORGANIC LIQUIDS

CROSS-REFERENCE TO RELATED APPLICATIONS

This application is a continuation of U.S. patent application Ser. No. 14/209,228, filed Mar. 13, 2014, which in turn claims priority to U.S. Patent Application Ser. No. 61/783,598, filed Mar. 14, 2013, the disclosures of which are incorporated herein by reference in their entireties for all purposes.

BACKGROUND OF THE INVENTION

There is an extensive body of literature on the purification of organic compounds especially in the practice of the removal of water from organic liquids. See, e.g., Williams et al., J. Org. Chem. 75:8351-4 (2010); Maslan et al., J. Phys. Chem. 60(8):1146-7 (1956). Conventional processes include distillation, use of dehydrating agents, and recrystallization, which are used alone or in combination. However, distillation is ineffective for organic liquids that form lower boiling azeotropes. Azeotropic distillation results in the formation of byproducts that are used to break the azeotrope. For example, benzene and toluene are used for the azeotropic distillation of ethanol resulting in hazardous waste mixtures of benzene/water and toluene/water requiring further treatment. Dehydrating agents such as alumina, magnesium sulfate, molecular sieves and sodium sulfate are also established methods for removal of water from organic liquids and from solutions of solutes in organic solvents.

For example, acetonitrile is a polar solvent with a high dielectric constant that has a strong affinity for polar compounds, such as organometallic complexes, metal chelates, ion pairs and organic solutes. Acetonitrile is miscible with water in all proportions. Acetonitrile is an excellent organic solvent and has become widely used in organic synthesis and manufacturing, as well as for purity and quality control analysis of organic compounds used in pharmaceuticals, cosmetics, personal care products and many other applications in research and development. In the latter aspects, the miscibility of acetonitrile in water renders it one of the most useful solvents for reverse phase high pressure liquid chromatography (RP-HPLC). Several events have resulted in a shortage in acetonitrile causing prices of this solvent to rise dramatically. See, e.g., Majors, et al., LC-GC North America 27:458-71 (2009); McConvey et al., Org. Proc. Res. Dev. 16:612-24 (2012); and Venkatasami, Sowa, Anal. Chim. Acta 665:227-30 (2010). Thus, there is unprecedented interest in the recovery of acetonitrile from research and manufacturing and RP-HPLC waste streams. However, like many other organic solvents, acetonitrile forms an azeotrope with water, which as persons skilled in the art appreciate, is a liquid mixture the individual components of which cannot be separated from each other by distillation. According to the literature, since the azeotrope boils at 76° C. and is composed of 86% acetonitrile and 14% water, there is no possibility of obtaining acetonitrile of purity above 86% by distillation and more costly processes are required to purify acetonitrile to a level higher than the azeotrope.

U.S. Patent Application Publication 2009/0090894, to Wang et al., teaches a method for separating acetonitrile from water that utilizes a saccharide (monosaccharide or disaccharide), and that the acetonitrile in the so-called "sugared-out" upper phase can reach a purity of 95.4%.

Notwithstanding a greater need for recycling, concern persists that unimpeded use of our natural resources is wasting essential resources and contributing toward global warming which if unchecked, will dramatically impact daily life. Emergent initiatives known as "sustainable manufacturing", "sustainability", "green manufacturing", "green technology" and "green chemistry" are designed to encourage better and more economical use of natural resources and to minimize any negative impact on the environment. They also aim towards making manufacturing process more economical, reducing costs of disposal through recycling and providing "green" products. In the area of chemical manufacturing there is a great need to improve research and manufacturing processes by developing new sustainable, green chemical processes (Anastas, Warner "Green Chemistry Theory and Practice", Oxford, 2000).

BRIEF SUMMARY OF THE INVENTION

The present invention is directed to a method of separating water from a composition containing an organic liquid and water, which entails adding to the composition a polyol that causes separation of the composition into at least two phases, wherein the first phase is aqueous and the second phase is organic (e.g., greater than about 80% pure organic liquid).

The methods of the present invention are advantageous in several respects. The extraction agents, i.e., the polyols, are (with rare exception) non-toxic, freely available, inexpensive, easy to use and reusable. More specifically, the "green" properties of polyols are exploited. With the arguable exception of ethylene glycol, they are non-toxic as indicated by their $LD_{50}$ values (ethylene glycol (8.5 g/kg), propylene glycol (25 g/kg), glycerol (greater than 20 g/kg), xylitol (22 g/kg), sorbitol (16 g/kg)). In addition, they are biodegradable and recyclable. Further, the high boiling points of polyols (e.g., ethylene glycol is 196-198° C.; propylene glycol is 187° C. and glycerol is 180° C. at 20 mmHg) facilitate their recovery by distillation of the more volatile components that include residual organic liquid and water. Polyols which are solid at room temperature may be also recovered by distillation of the more volatile components and recrystallization.

As shown in the working examples, the present invention is successful in extracting water from various organic liquids such as acetonitrile to achieve purity levels that reach about 98% or greater and the polyol is recovered in greater than about 95% yield.

DETAILED DESCRIPTION

Broadly, the present invention may be used to separate any organic liquid from water, provided that upon contact with the polyol, a phase separation occurs. Without intending to be bound by any particular theory of operation, the present inventors believe that phase separation occurs via a competition between the organic liquid and the polyol for water. When the strength (as indicated by enthalpy or free energy) of the interaction between the polyol and water is greater than that of the organic liquid and water, phase separation occurs resulting in an aqueous phase and an organic phase. The aqueous phase contains water and polyol and has lesser amounts of the organic liquid than the amount originally present in the composition. The organic phase typically contains substantially the organic liquid which for purposes of the present invention means that the organic phase typically contains relatively smaller amounts of water, e.g., less than about 20%, 15%, 10%, 5% or less Water is frequently difficult to remove from organic liquids. The present method provides a practical solution in that the water content in the original composition is substantially reduced on addition of the polyol to obtain an organic liquid of suitable purity to enable it to be recycled. The polyol can be also recovered for re-use. Moreover, the invention may also be viewed as a practical way to purify water when it is present in admixture with an organic liquid such that the water can be subjected to further treatment for re-use or for environmentally responsible disposal.

Formally the phase separation process is an equilibrium process where the Gibbs Free Energy equation applies (e.g., 1):

$$\Delta G = \Delta H - T \Delta S \tag{1}$$

where $\Delta$ is the observed change from the initial state to the state at equilibrium, G is defined as the free energy, H is the enthalpy, T is temperature given in Kelvin, and S is entropy.

The phase separation reaction is given by the following reaction equation (eq 2):

$$Org_{(aq)} + P_{(l)} \rightleftharpoons Org_{(l)} + P_{(aq)} \tag{2}$$

where Org is the organic liquid, P is the polyol, (l) indicates a pure liquid phase or, if appropriate (s) in the case of a pure solid phase, (aq) indicates aqueous solution, respectively, of the organic liquid or polyol.

Thus, the equilibrium constant for phase separation ($K_{PS}$) is given by eq 3:

$$K_{PS} = \frac{[Org_{(l)}][P_{(aq)}]}{[Org_{(aq)}][P_{(l)}]} \tag{3}$$

where, for example, the brackets [Org$_{(aq)}$] indicate concentration of the organic liquid; however, concentration terms are often expressed as activity (Moore, "Physical Chemistry, 3rd ed.," Prentice Hall, 1963, p. 349), i.e., $^a$Org$_{(aq)}$. By definition, a pure liquid or solid has an activity of 1. Thus, eq 3 reduces to eq 4.

$$K_{PS} = \frac{[P_{(aq)}]}{[Org_{(aq)}]} \tag{4}$$

As indicated by the Gibbs equation (eq 5), an increase in $K_{PS}$ leads to a more negative value of $\Delta G$ which is interpreted as a decrease in free energy. Thus, phase separation is driven by a decrease in free energy of the reaction.

$$\Delta G = -RT \ln K_{PS} \tag{5}$$

where R is the gas constant 8.314 J/T, mole, J is Joules and T is temperature in Kelvin (K)

Persons skilled in the art may determine whether a given polyol will cause phase separation in a composition containing water and a given organic liquid by employing Le Chatelier's Principle (Umland, Bellama, "General Chemistry, 3rd ed.," Brooks/Cole, 1999) to drive the equilibrium in eq 2 toward the products ("to the right"). According to Le Chatelier's Principle, factors that control this equilibrium process are: a) free energy of the interaction of water with the organic liquid and water with the polyol (which can be roughly estimated by one skilled in the art by solubility), concentration and temperature. If the solubility of the organic liquid in water is low, the reaction (eq 2) will be driven to the right. If the solubility of the polyol in water is high, the reaction will be driven to the right. Furthermore, if the solubility of the polyol in the organic liquid is low, the reaction will also be driven to the right. An increase in concentration of the organic liquid and polyol relative to water will drive the reaction to the right. A decrease in temperature will decrease the free energy of interaction between water and the organic liquid and, thus, increase phase separation.

Broadly, the organic liquids from which water can be extracted are those in which water is at least partially soluble and which form a single homogeneous phase when mixed with water. Suitable organic liquids include industrial solvents which, because of their expense and environmental toxicity, are candidates for recycling. The organic liquids also include solvents, reagents and intended or unintended byproducts, used or generated in research and development. The organic liquids further include industrial products such as oil, petroleum, petroleum distillates, and fuels such as gasoline, kerosene, diesel and biodiesel.

Organic liquids suitable for use in the present invention can be categorized into three basic classes: non-polar ("np"), polar aprotic ("pap," which as known in the art, do not have a labile proton) and polar protic ("pp," which as known in the art, have a labile proton that can be donated to a reagent) (Reichardt, "Solvents and Solvent Effects in Organic Chemistry, 2nd ed.," VCH, 1990). The miscibility of the organic liquid in water is not critical provided that a phase separation occurs, the present method can separate organic liquids that are only slightly miscible with water to those that are completely miscible with water.

Representative examples of non-polar organic liquids that may be suitable for use in the present invention include hexanes, cyclohexane, carbon tetrachloride, emulsified crude oil, crude oil, gasoline, kerosene, petroleum, petroleum distillates, biodiesel, and diesel fuel, all of which have slight miscibility with water. For example, the organic liquid, hexanes, is a mixture of isomers having the formula $C_4H_4$. Hexanes are miscible with water in very small proportions (1.1 g/100 mL, Riddick, Bunger, "Organic Solvents, Physical Properties and Methods of Purification, 3rd ed., Vol. II," Wiley, 1970, p. 78-79). It is frequently necessary for purposes of recycling and for practical use as an anhydrous solvent and for chemical reactions including combustion to remove even traces of water that are present in these liquids.

Representative examples of polar aprotic organic liquids that may be suitable for use in the present invention include dibutylphthalate, dimethylphthalate, t-butylmethylether, mesitylene, toluene, benzene, p-xylene, diethyl ether, chloroform, ethyl acetate, propylene carbonate, 1,2-dimethoxyethane, methyl benzoate, tetrahydrofuran, 2-methyltetrahydrofuran, halogenated alkanes such as dichloromethane, cyclopentanone, 2-butanone (methylethylketone), nitromethane, acetone and cyanated alkanes such as acetonitrile and propionitrile. Acetonitrile is an excellent example of a polar aprotic organic liquid that is completely miscible with water. Acetone, dioxane, and tetrahydrofuran are also completely miscible with water. Examples of polar aprotic organic liquids that are only partially miscible with water include dichloromethane and chloroform (in which only traces of water dissolve). Water dissolves to a greater extent (e.g., greater than 1 to 10% wt/v) in organic liquids such as diethyl ether, ethyl acetate, benzene and toluene.

Representative examples of polar protic organic liquids that may be useful in the practice of the present invention include alkanols, e.g., 1-octanol, cyclohexanol, isopentanol (3-methyl-1-butanol), 2-pentanol, 1-butanol, t-butanol, 1-propanol and isopropanol (2-propanol). Alkanols are a broad class of organic liquids that are pp and range from completely miscible with water to partially miscible. Those that are completely miscible include methanol, ethanol, 1-propanol, isopropanol (2-propanol), t-butanol. Those that are partially miscible include 1-butanol, 2-butanol, pentanol, cyclopentanol, cyclohexanol, hexanol, heptanol, and 1-octanol.

Polyols useful as extraction agents in the present invention may be described in terms of the general formula:

$$R^1(CHOR^3)(CH_2)_x(CHOR^3)_y(CH_2)_z(CHOR^3)R^2$$

wherein $R^1$ and $R^2$ each independently represent hydrogen, a linear or branched $C_1$-$C_8$ alkyl (e.g., methyl, ethyl) group or an aryl group (e.g., phenyl and naphthyl), or $R^1$ and $R^2$ taken together represent a bond such that the polyol is cyclic; wherein x, y and z are each independently integers including 0 to 4, and wherein the sum of x+y+z is less than or equal to 4 (i.e., 0, 1, 2, 3, or 4), provided that when $R^1$ and $R^2$ taken together represent a bond, the sum of x, y, and z is 4; and $R^3$ represents hydrogen when y is 1, and when y is 2, 3 or 4, each $R^3$ is hydrogen or one of the $R^3$ groups is pyranosyl or polypyranosyl and the other one, two, or three $R^3$ groups is hydrogen (i.e., in some embodiments is only hydrogen and in some embodiments $R^3$ is one pyranosyl or one polypyranosyl group and the remaining $R^3$ groups are hydrogen). As persons skilled in the art appreciate, hydrogenation of disaccharides such as maltose and lactose produces polyols that are linked to one pyranosyl group via an internal or terminal hydroxyl group namely pyranosyl-substituted polyols. In addition, hydrogenated polysaccharides produce polyglycitols such as Maltotriitol, Maltotetraitol and hydrogenated starch hydroxylate (polyglucitol) namely polypyranosyl-substituted polyols. Moreover, persons skilled in the art appreciate that when $R^1$ and $R^2$ together represent a bond, the polyol is cyclic e.g., an inositol. The pyranose-substituted polyols, polypyranosyl-substituted polyols, and inositols are considered polyols within scope of this invention. For purposes of the present invention, "polypyranosyl" refers to 2-4 pyranosyl groups linked together.

Figure 1A:
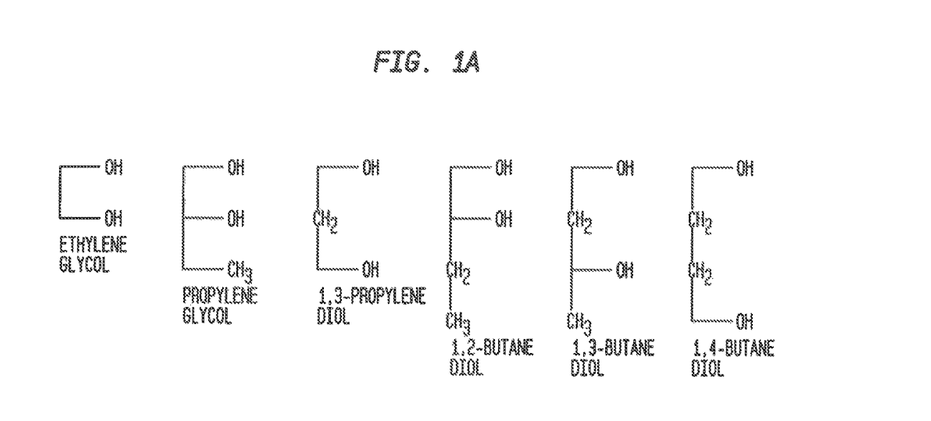
FIGS. 1A-D are schematic illustrations of structures of various polyols that may be useful in the practice of the present invention, wherein A shows $C_2$-$C_4$ diols; B shows $C_3$ triols to $C_6$ hexaols; C shows polyols having cyclic sugar (pyranosyl) groups; and D shows a representative cyclic polyol, inositol.
Figure 1B:
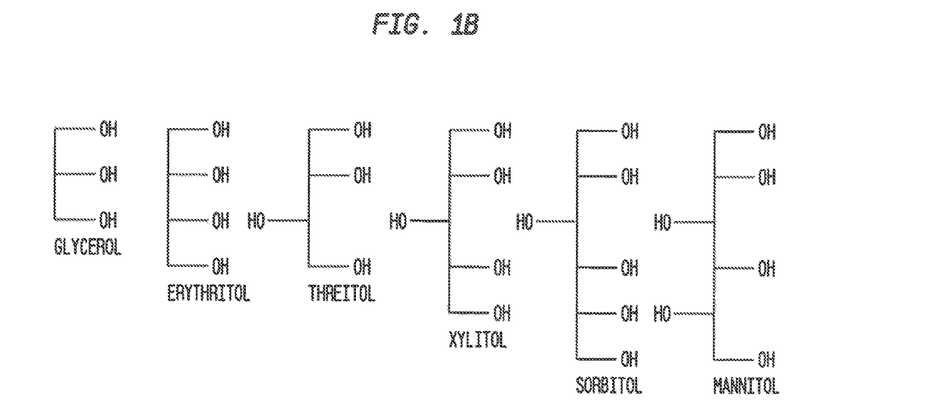

As shown in FIGS. 1A-D, the polyol moieties in this formula are indicated as "CHOW" groups when $R^3$ represents OH. These groups may be linked to each other in a continuous fashion from the initial carbon atom to the last carbon atom in the chain. The simplest polyol applicable to the general formula is ethylene glycol as shown in FIG. 1A where $R^1$ and $R^2$ are H, $R^3$ is OH, and subscripts x, y and z are 0. In addition, there may be an alkyl group (R') at the beginning of the chain where, for example, $R^1$ is methyl as in the case of propylene glycol (FIG. 1A). In the case of 2,3-butanediol (not shown), $R^1$ is methyl, $R^3$ is OH, x, y, and z are each zero, and $R^2$ is methyl. Methylene $(CH_2)_y$ groups may also be present between the "CHOH" moieties where subscript x indicates the number of methylene groups. In the case of 1,3-propanediol, x is 1 (FIG. 1A). In the case, of 1,4-butanediol, x is 2 (FIG. 1A).

Figure 1C:
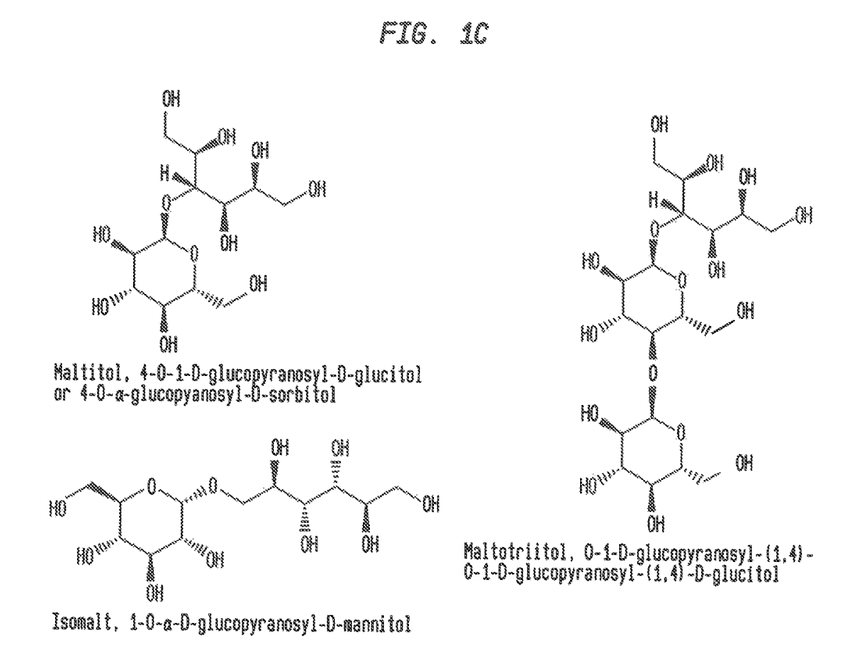
Figure 1D:
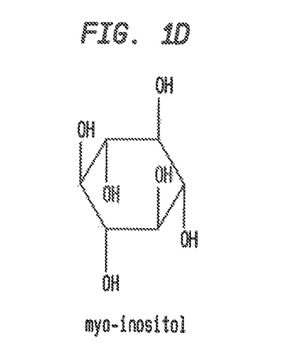

Glycerol (FIG. 1B) contains three contiguous "CHOH" moieties. In the case of sorbitol (FIG. 1B), there are six contiguous "CHOH" moieties where $R^1$ and $R^2$ are H; x and z are 0, y is 4 and $R^3$ is OH. Additional polyols schematically illustrated in FIG. 1B include erythritol, threitol, xylitol, and mannitol. Polyols included in this invention may contain a pyranosyl such as glucopyranosyl or a polypyranosyl moiety connected to one of the hydroxyl groups of the linear polyol chain. As shown in FIG. 1C, the pyranosyl polyols, Maltitol and Isomalt, and polypyranosyl-substituted polyol, Maltotriitol, may also be useful in the practice of the present invention. Examples of other polypyranosyl-substituted polyols that may be useful include Maltotetraitol and polyglucitol. Cyclic polyols, inositol (also known as myo-inositol) that may be useful is shown in FIG. 1D.

Ethylene glycol, propylene glycol and glycerol as well as other polyols useful in the present invention are liquids at room temperature, which is advantageous in that they are easily poured or pumped into a reaction vessel. Moreover, these liquids more readily dissolve and/or are dispersed in organic liquids. Even though other polyols such as erythritol, xylitol, sorbitol, mannitol and Isomalt are solid at room temperature, they are also applicable in this invention. Although solid polyols require time and heat to dissolve in an organic liquid, in some cases, they are more effective than the liquid polyols.

Figure 2:
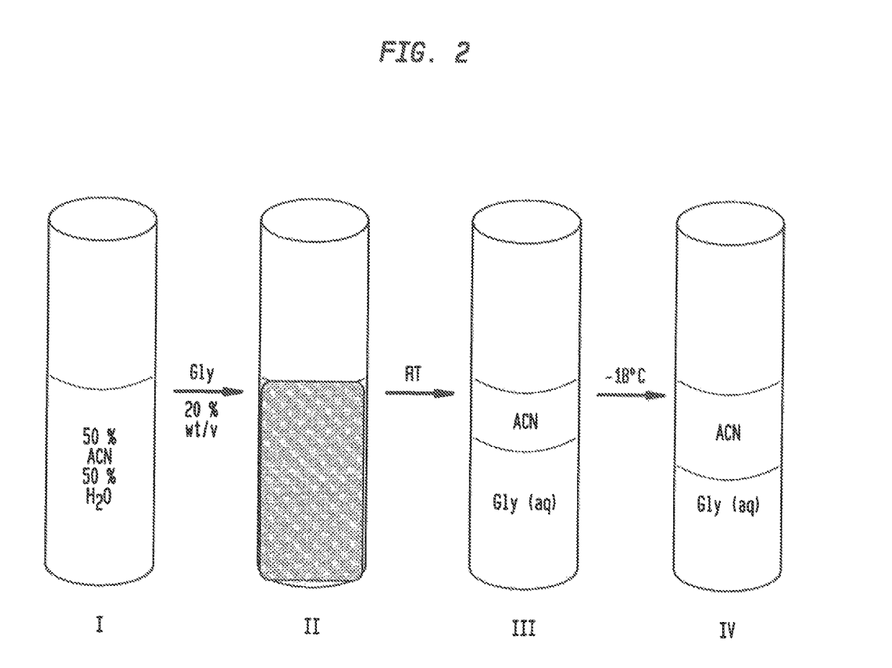
FIG. 2 illustrates a schematic flow diagram of an exemplary embodiment of the present invention.

As illustrated in FIG. 2, phase separation may be easily monitored by visual inspection as the refractivity of the organic layer is different from the aqueous layer. Initially, on mixing the polyol into the composition of the organic liquid (I), the organic liquid is rendered insoluble and the mixture becomes cloudy (II). The amount of the polyol sufficient to cause the composition to become cloudy is called the "cloud point" as that term is understood in the art. See Imani et al., J. Chem. Thermodynamics, 41:893-6 (2010). In a few minutes, the cloudy mixture begins to separate forming an aqueous and an organic layer (III). In some embodiments, cooling may cause the phase separation to increase (IV). Phase separation may be more easily visualized by using a dye such as Sudan IV which stains the organic phase red and does not stain the aqueous phase. Alternatively, fluorescein can be used to stain the aqueous phase fluorescent green.

The amount of polyol used in the methods of the present invention depends on variables such as the nature of the organic liquid, the percentage of water in the composition containing the organic liquid, the specific polyol used as the extraction agent, and the total volume of the composition from which the organic liquid is to be separated. Typically, the compositions containing water and the organic liquid that are generated from industrial or research processes (e.g., water/acetonitrile mixtures generated from high pressure liquid chromatographic procedures) contains about 30 to about 90% organic liquid. The methods of the present invention may be effective in extracting about 80 to about 99% of the water, thus generating organic liquids having about 80 to about 99% purity.

Evaluation of solubility of water in an organic liquid may be readily assessed by one skilled in the art by performing a solubility test. Also, extensive data on water solubility are available in the literature (See: a) The Merck Index, 12th Ed., and, b) Reichardt, "Solvents and Solvent Effects in Organic Chemistry, 2nd ed.," VCH, 1990). In general, in embodiments where the water is very slightly miscible with the organic liquid, the amount of the polyol typically ranges from about 0.01 to about 1% wt/v of the polyol relative to the amount of water in the composition. In these cases, where water concentration is very low, it may be advantageous to use an excess of the polyol relative to the amount of water present where a convenient amount is 5% wt/v. In embodiments where water is partially or infinitely miscible with the organic liquid, the amount of polyol typically ranges from about 5 to about 10% wt/v, from about 10 to about 25% wt/v and from 25-50% wt/v relative to the total volume of the composition, e.g., where the preferred range is about 10% to about 25% wt/v.

Water concentration in the final product (e.g., either the aqueous or organic phase) can be easily determined by persons skilled in the art using standard techniques such as Karl-Fischer titration, nuclear magnetic resonance (NMR) spectroscopy (e.g., quantitative NMR), density measurements, and infrared spectroscopy preferably with an attenuated total reflectance probe (ATR-IR) (Kassis, Bhawtankar, and Sowa, J. Pharm. Biomed. Anal., 53:269-273 (2010)). By way of illustration, the purity of the resultant acetonitrile layer may be determined over the spectral range of 4000 to 600 $cm^{-1}$. Within this range, key absorbances are 1640 $cm^{-1}$ ($H_2O$, bending vibrational mode), 3500 $cm^{-1}$ (OH stretch) and 2250 $cm^{-1}$ (C-triple bond-N stretch of acetonitrile).

As disclosed above and illustrated in FIG. 2, in some embodiments, lowering the temperature increases the phase separation and thus the amount of water extracted. In general, the extraction may be conducted at a temperature between about 40° C. and about −78° C., and in some embodiments from about 25° C. to about 2° C., and in other embodiments, from about 25° C. to about −25° C. In the upper end of the range, phase separation is observed with solid polyols in which the composition is heated to dissolve the polyol. In the low end of the range, the temperature may be lowered such that the aqueous layer freezes; however, the temperature must be above the freezing point of the organic liquid such that the organic liquid remains as a liquid. In some embodiments, once a phase separation is obtained, the composition of the phase remains stable even when warmed to room temperature. Examples include acetonitrile/glycerol, acetonitrile/xylitol, acetonitrile/sorbitol, and isopropyl alcohol/sorbitol. This phenomenon is advantageous as the phase separation may be optimized at low temperature and then stored at room temperature until the layers are mechanically separated. In some embodiments, the phases are not temperature stable. Thus, once phase separation is obtained at low temperature, mechanical separation must be performed at low temperature. Examples include acetonitrile/ethylene glycol, and acetonitrile/propylene glycol, acetonitrile/mannitol, and acetone/sorbitol.

Other operating parameters, e.g., pH and pressure, at which the present methods are conducted, are not considered critical. The volume of the original composition may affect the amount of polyol used. For instance, in some embodiments, relatively small volumes of the composition may require slightly more polyol to maximize phase separation relative to large volumes. As described in the working examples (Table 3), a 10 mL volume of acetonitrile/water (50% v/v) at room temperature 21% wt/v glycerol gave maximum phase separation, whereas for a 1 L volume of the same, 17% wt/v of glycerol gave maximum phase separation. Without intending to be bound by any particular theory of operation, the present inventors believe that the relationship between volume and maximum phase separation is related to the surface of the reaction vessel which may compete with binding of the polyol. In this regard, addition of glass beads to a composition requires that more of the polyol be added to the composition to induce phase separation. In addition, slightly more polyol (1-5% wt/v) is required when a glass vessel is used versus a polypropylene vessel.

Depending on these other variables, the amount of time required for optimal extraction may also vary, generally between about 2 min and about 2 hours for separations conducted at room temperature and from about 1 hour to about 12 hours for separations that require cooling. In some embodiments, separations with high viscosity liquids (greater than about 1000 poise) such as diesel fuel, petroleum distillates and cyclohexanol, about 12 hours to about 48 hours may be required for separation or use of centrifugation may be necessary.

Figure 3:
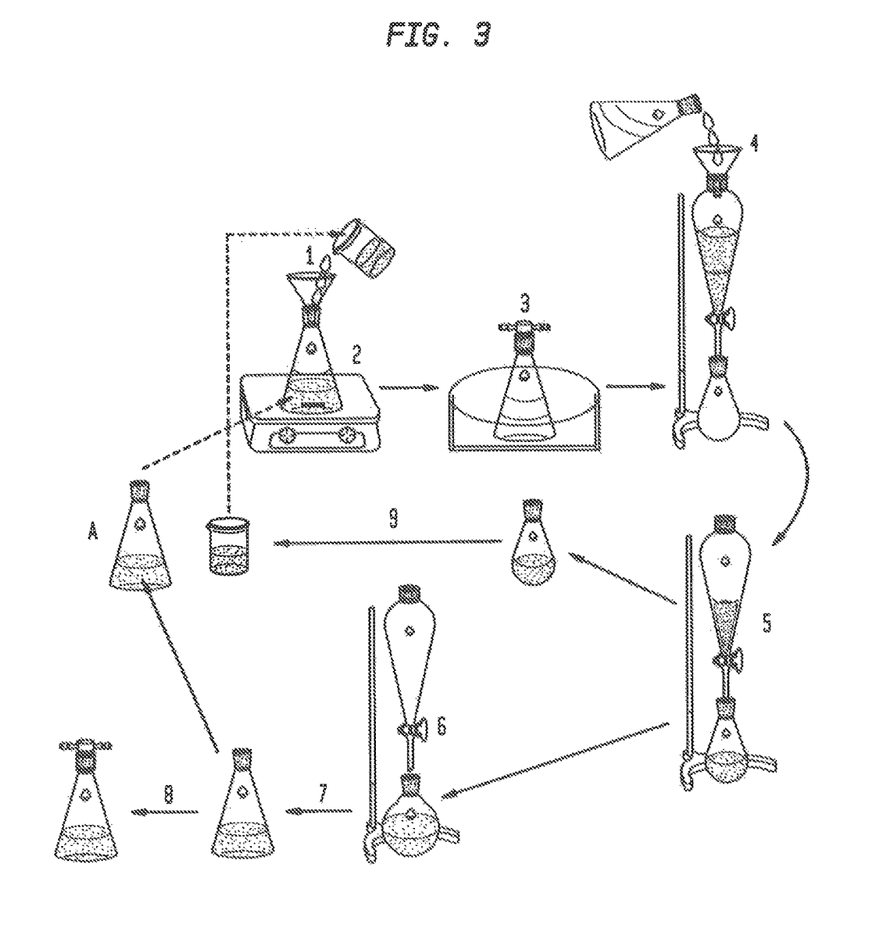
FIG. 3 is a schematic diagram illustrating an embodiment of a polyol-induced extraction (PIE), in accordance with the present invention, which can be conducted manually.

An embodiment of the present invention is now illustrated by reference to FIG. 3, which features a separation performed manually in 9 steps, for example, in a research laboratory setting. A composition of organic liquid containing water (Erlenmeyer flask) and a liquid or solid polyol (beaker) is obtained (A). In Step 1, the polyol is added to the composition, and, in step 2, the polyol is mixed into the composition such that the polyol dissolves or is dispersed in the composition. If the polyol is a solid, the mixture is heated to reduce the time it takes to dissolve the polyol. At this point, separation may spontaneously occur. In Step 3, the composition containing the polyol is cooled below room temperature to increase separation or to induce separation if it has not already occurred. In Step 4, the phase separated mixture is poured into a separatory funnel. In Step 5, one skilled in the art may easily determine the whether the upper or lower phase contains the organic liquid. Assuming that the upper phase is the desired organic phase (due to its lower density), the lower phase is drained into a round-bottomed flask and, in step 6, the upper phase is drained into a different round-bottomed flask. In Step 7, the organic phase is distilled by simple, fractional or vacuum distillation (e.g., using a rotary evaporator) to obtain a pure organic liquid (typically, greater than about 95% purity, less than about 5% water). In Step 8, if the organic phase is of insufficient purity, e.g., typically containing greater than about 5 to 25% water, it is subjected to additional treatments with the polyol. In Step 9, the polyol is recovered from the aqueous solution by distillation or recrystallization and may be used again for PIE.

Figure 4:
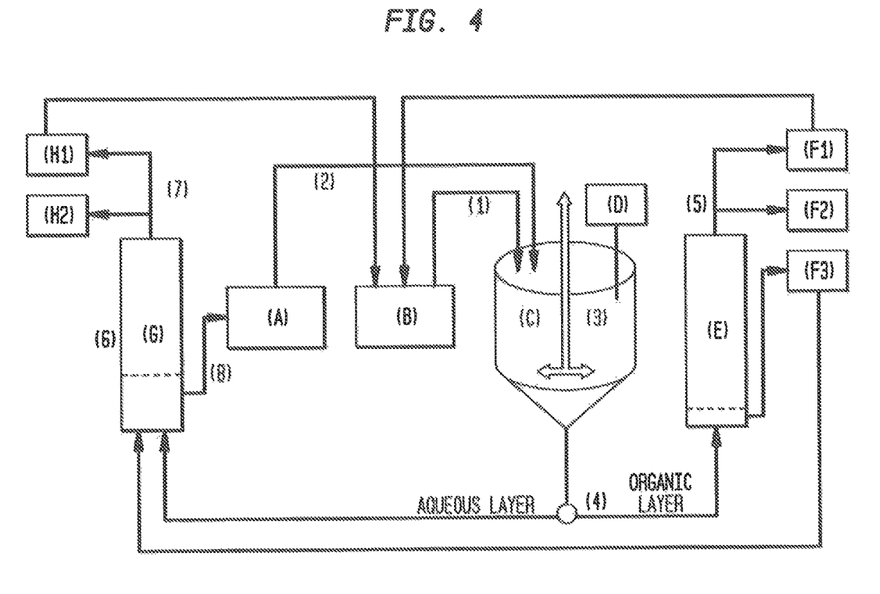
FIG. 4 is a schematic diagram illustrating an embodiment of the PIE process, in accordance with the present invention, which may be conducted on an industrial scale. The diagram is specifically illustrated for glycerol-induced extraction of water from acetonitrile.

An embodiment of the invention is now illustrated in by reference to FIG. 4, which is described in the context of the glycerol-induced extraction of water from a composition containing water and acetonitrile (ACN) on an industrial scale. In step 1, the acetonitrile/water mixture is added to Reaction Vessel C. In step 2, glycerol is added to Reaction Vessel C. In step 3, the acetonitrile/water and glycerol components are mixed. In step 4, one skilled in the art may easily substitute glycerol for another liquid polyol or for a solid polyol. However, if the polyol is a solid, the mixture is heated as needed for dissolution of the polyol. The mixture is cooled to induce separation or to increase separation as needed. Reaction Vessel C also enables contents to settle into distinct aqueous and organic phases. The phases are either detected by visual inspection or through the use of a sensor such as an ATR-IR probe. The sensor will also allow for determination of the purity of each phase or aliquots can be withdrawn to determine the composition. In step 5, the aqueous layer and organic layer are directed to the respective distillation apparati I and II. In cases where the aqueous layer is more dense than the organic layer, such as acetonitrile, the aqueous layer will be the bottom layer. One skilled in the art will be able to determine cases where the aqueous layer is less dense than the organic layer, such as alkyl halides including dichloromethane, methyl iodide and carbon tetrachloride. In step 6, the organic layer containing acetonitrile is subjected to distillation. Fractions are collected such that impure lower boiling fractions containing acetonitrile/water are returned to B for further recovery; pure acetonitrile is collected in vessel E; residue in D containing glycerol is directed to distillation apparatus II for recovery of glycerol. In step 7, the aqueous layer containing mostly water, glycerol and smaller amounts of acetonitrile is subjected to distillation for recovery of glycerol. In step 8, the more volatile component of the distillate is collected and the distillate containing water is collected in vessel G. In step 9, glycerol is directed to vessel A for further use. If necessary, glycerol is removed for purification by distillation, recrystallization, charcoal treatment, etc., before it is directed to vessel A.

For purposes of the present invention, the term "about" means ±1, 2, 3, 4, 5, 6, 7, 8, 9, 10, 11, 12, 13, 14, 15, 16, 17, 18, 19 or 20% of the numerical value with which it is used.

The present invention will now be described in terms of the following, non-limiting examples.

Example 1. Evaluation of Suitability of Organic Liquids for PIE

To a 35 mL culture tube was added 10 mL of the organic liquid. To aid in observation of the phase separation a trace (less than 1 mg) of Sudan IV was added which stained the organic liquid red. Water was added by dropwise addition until the organic liquid was saturated with water. If the organic liquid was completely miscible with water then only 2.5 to 10 mL of water was added to make 20-50% aqueous solutions. To these solutions, was added 20% wt/v of the polyol. The culture tube was capped and the contents were mixed to dissolve the polyol. For solid polyols, the culture tube was heated with warm tap water (40-50° C.) until the solid dissolved. If the organic liquid was partially miscible with water such that such that saturation was obtained with 5-20% water, 20% wt/v of the polyol was also added. If the organic liquid was slightly miscible with water such that such that saturation was obtained with one drop of water (0.05 to 0.1 mL), then only 5% wt/v of the polyol was added. The mixtures were allowed to settle at room temperature for 5 to 10 min and phase separation was observed by the formation of a distinct aqueous and organic phase wherein the organic phase was stained red and the aqueous phase was clear and colorless. If phase separation did not occur at room temperature (RT), then the culture tube was placed in the refrigerator (2° C.) or the freezer (−18° C.) for 12 h (overnight) and evaluated for phase separation. The results are shown in Table 1.

TABLE 1

Organic Liquids Tested for Polyol-induced Extraction (PIE).

| Organic Liquid | Type[a] | Gly Solubility[b] | Composition (% $H_2O$)[c] | Polyol[d] | wt/v[e] Temp[f] |
|---|---|---|---|---|---|
| dimethylsulfoxide | pap | s | 50% | nr | |
| poly(ethylene glycol)butyl ether | pap | s | 50% | nr | |
| Acetonitrile | pap | i | 20% | EG | 20, −18° C. |
| | | | 20% | PG | 20, −18° C. |
| | | | 50% | Gly | 20%, RT |
| | | | 50% | Ery | 20%, RT |
| | | | 50% | Xyt | 20%, RT |
| | | | 50% | So | 20%, RT |
| | | | 50% | Man | 1%,[g] −10° C. |
| | | | 50% | Isom | 20%, RT |
| | | | 50% | Malt | 20%, RT |
| | | | 50% | Ino | nr |
| dimethylformamide | pap | s | | nr | |
| N-methylpyrolidinone | pap | s | | nr | |
| dimethylacetamide | pap | s | | nr | |
| tri(ethylene glycol) | pp | s | | nr | |
| 2-butanone | pap | i | 50% | Gly | 20, RT |
| acetone | pap | s | 40% | So | 20%, −18° C. |
| cyclopentanone | pap | i | 50% | Gly | 20%, RT |
| 2-ethoxyethanol | pap | s | | nr | |
| t-butanol | pp | s | 25% | Gly | 30, −18° C. |
| 1-butanol | pp | i | 25% | Gly | 20%, RT |
| | | | | So | 20%, RT |
| isopentyl alcohol (3-methyl-1-butanol) | pp | s | 50% | Gly | 20%, RT |
| cyclohexanol | pp | s | ~10% | Gly | 20%, RT |
| 1-octanol | pp | i | sat | Gly | 5%, RT |
| pyridine | pap | s | | nr | |
| dichloromethane | pap | i | sat | Gly | 5%, RT |
| tetrahydrofuran | pap | s | 20% | Gly | 20%, −18° C. |
| tri(ethylene glycol) dimethyl ether | pp | i | | nr | |
| 1,2-dimethoxyethane | pap | i | ~10% | Gly | 20%, RT |
| methyl benzoate | pap | i | sat | Gly | 5%, RT |
| propylene carbonate | pap | i | sat | Gly | 5%, RT |
| ethyl acetate | pap | i | sat | Gly | 5%, RT |
| | | | | So | 5%, RT |
| chloroform | pap | i | sat | Gly | 5%, RT |
| diethyl ether (ethyl ether) | pap | ss | sat | Gly | 5%, RT |
| | | | | So[h] | 5%, RT |
| mesitylene | pap | i | sat | Gly | 5%, RT |
| p-xylene | pap | i | sat | Gly | 5%, RT |
| benzene | pap | i | sat | Gly | 5%, RT |
| toluene | pap | i | sat | Gly | 5%, RT |
| | | | | So | 5%, RT |
| carbon tetrachloride | np | i | sat | Gly | 5%, RT |
| | | | | So | 5%, RT |
| t-butylmethyl ether | pap | ss | sat | Gly | 5%, RT |
| dimethylphthalate | pap | i | sat | Gly | 5%, RT |
| dibutylphthalate | pap | i | sat | Gly | 5%, RT |
| crude oil(petroleum) | | i | sat | Gly | 5%, RT |
| emulsified crude oil | | | | Gly | 5%, RT |
| gasoline | np | i | sat | Gly | 20%, RT |
| | | | | So | 20%, RT |
| kerosene | np | i | sat | Gly | 20%, RT |
| | | | | So | 20%, RT |
| diesel | np | i | sat | Gly | 20%, RT |
| | | | | So | 20%, RT |
| petroleum distillates | np | i | sat | Gly | 20%, RT |
| | | | | So | 20%, RT |
| cyclohexane | np | i | sat | Gly | 5%, RT |
| | | | | So | 5%, RT |
| hexanes | np | i | sat | EG | 5%, RT |
| | | | | PG | 5%, RT |
| | | | | Gly | 5%, RT |
| | | | | So[g] | 5%, RT |

TABLE 1-continued

Organic Liquids Tested for Polyol-induced Extraction (PIE).

| Organic Liquid | Gly Solu- bility[b] | Compo- sition (% H$_2$O)[c] | Pol- yol[d] | wt/v[e] Temp[f] |
|---|---|---|---|---|
| | | | Man | 1%, RT |
| | | | Ino | 1%, RT |

[a]Type of organic liquid; pap is polar aprotic; pp is polar protic; np is nonpolar.
[b]Solubility of glycerol in the pure organic liquid at RT.
[c]% of water in the organic liquid/water composition. If sat (saturated) is stated, water is ≤1%.
[d]nr is no separation observed at RT on addition of greater than 20% Gly and on cooling to −18° C. Polyols are ethylene glycol (EG), propylene glycol (PG), glycerol (Gly), erythritol (Ery), xylitol (Xyl), sorbitol (So), mannitol (Man), Isomalt (Isom), Maltitol (Malt), inositol (Ino).
[e]Amount of polyol added (wt) relative to the volume (v) of the composition to initiate phase separation.
[f]Initial addition of polyol was at RT (room temperature), cooling to −18° C. was done if separation was not initially observed at RT.
[g]Amount of mannitol is limited due to low solubility.
[h]On addition of sorbitol, a viscous aqueous solution was formed.

Example 2. Determination of Amount of Glycerol Required to Obtain Maximum Phase Separation of Different Compositions of Acetonitrile/Water Mixture by Titration Six glass vials were prepared each containing a 10 mL (v/v) mixture of 95%, 90%, 75%, 50%, 25%, and 10% of acetonitrile in water, respectively. Glycerol was added in incremental aliquots at room temperature. The mixtures were shaken and observed for minimum amount of glycerol required for maximal phase separation. The mixtures were then cooled in freezer at −18° C. overnight for further separation and analyzed for percent purity of acetonitrile by ATR-IR spectroscopy in the upper layer of the separated phases.

Figure 5:
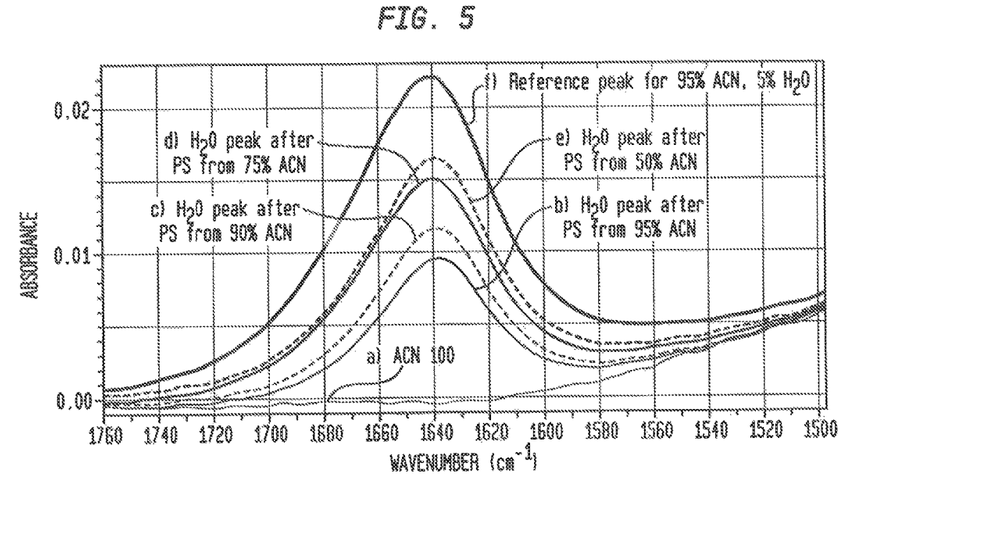
FIG. 5 is a graph showing an infrared spectral analysis series of the acetonitrile (ACN) layer of glycerol-induced phase separation (PS), wherein water concentration was monitored by measuring the peak area at 1640 cm$^{-1}$.

The results are listed in Table 2. A spectral analysis is presented in FIG. 5, which shows a cut out of the 1640 cm$^{-1}$ absorbance wherein the amount of water in the resulting acetonitrile layer is less than 5% for four treatments of acetonitrile/water mixture with glycerol.

TABLE 2

Minimum amount of glycerol required for maximum phase separation of acetonitrile and water.

| entry | Percent composition of ACN[a] (v/v) | Minimum amount(g) of Gly[a] for maximum PS[a] | % Gly at maximum PS (wt/v %) | % purity[b] of ACN, after cooling to −18° C. |
|---|---|---|---|---|
| 1 | 95 | 0.8 | 8 | 98% |
| 2 | 90 | 1.0 | 10 | 98% |
| 3 | 75 | 1.4 | 14 | 97% |
| 4 | 50 | 1.8 | 18 | 97% |
| 5 | 25 | More than 10 g | More than 100% | NA |
| 6 | 10 | More than 10 g | More than 100% | NA |

[a]ACN is acetonitrile; Gly is glycerol; PS is phase separation.
[b]Purity determined by ATR-IR (see FIG. 5).

These results clearly indicate the amount of polyol for optimal separation depends on the % water in the original composition as illustrated by the successful extraction of water from acetonitrile by glycerol from compositions ranging from 5-50% v/v water. Above 75% v/v water, separation was not observed at room temperature.

Example 3. Determination of the Effect of % Water and Temperature on Glycerol-Induced Extraction of Water from Acetonitrile Twelve plastic (polypropylene) graduated centrifuge tubes were prepared each containing 10 mL of 95%, 90%, 80%, 70%, 60%, 50%, 45%, 40%, 35%, 30%, 20%, and 10% acetonitrile/water (v/v), respectively. Control samples of 100% acetonitrile and 100% water were also prepared. To each tube was added 2.0 g glycerol (20% wt/v) and the mixtures were shaken. The mixtures were allowed to stand at room temperature (20° C.) for 15 min to allow phase separation to reach equilibrium. The volume of the upper acetonitrile phase was measured. The tubes were then cooled overnight to 2° C. and −18° C. and the volume of the upper phases was measured at each temperature.

Figure 6:
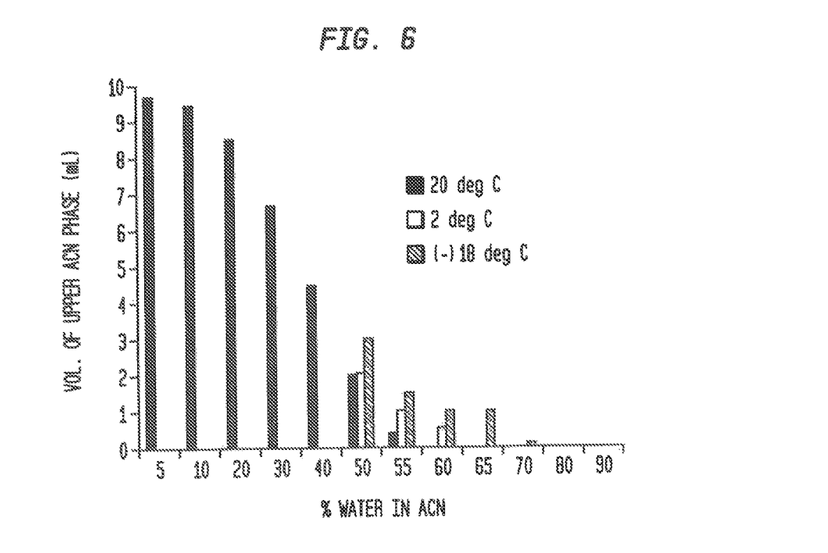
FIG. 6 is a bar graph demonstrating the effect of the amount % water and temperature on phase separation.

The results are illustrated by spectral analysis in FIG. 6. At room temperature, phase separation was observed at 55% water. However, decreasing temperature to 2° C. resulted in phase separation for 60% water and at −18° C., separation was observed at 70% water. At 55% water, there was an excellent indication of the effect of temperature. Surprisingly, at room temperature 0.4 mL of ACN was obtained. Lowering the temperature to 2° C. resulted in 1.0 mL and by lowering to −18° C., 1.5 mL was obtained.

Example 4: Glycerol-Induced Extraction of Water from Acetonitrile

To 1.0 L of a 1:1 mixture of acetonitrile and water was added 200 g of glycerol (20% w/v) and the mixture swirled until the glycerol dissolved. Initially, two layers formed consisting of acetonitrile as the less dense top layer and an aqueous solution of glycerol as the bottom layer. The mixture was placed in a freezer at −18° C. overnight in increase the phase separation. The cold mixture was poured into a separatory funnel and the bottom aqueous layer removed. The top layer resulted in 378 mL (75.6% yield) and contained 97% acetonitrile with 3% water. The top layer was treated again with glycerol 76 g (20% w/v), swirled and placed in freezer at −18° C. overnight for further separation of water. The cold mixture was again separated using a separatory funnel. The yield of the top layer was 355 mL (71%) and contained 98% acetonitrile, 1-2% water and 0.53% glycerol (1.9 g). This layer was distilled at atmospheric pressure and 99% pure acetonitrile was collected at 81° C. (352 mL, 70.4% yield). The glycerol was recovered by fractional distillation. Residual acetonitrile in the distillate was collected between 76-99° C. and water was collected at 100° C. leaving anhydrous glycerol in the distillation pot (190 g, 95% recovery).

Example 5: Sorbitol-Induced Extraction of Water from Acetonitrile

To 1.0 L of a 1:1 mixture of acetonitrile and water was added 200 g of sorbitol (20% w/v) and the mixture was swirled until the sorbitol dissolved. Initially, two layers formed—acetonitrile as the less dense top layer and an aqueous solution of sorbitol as the bottom layer. The mixture was placed in a freezer at −18° C. overnight. The cold mixture was poured into a separatory funnel and the bottom aqueous layer was removed. The yield of the top layer was 380 mL (76%) and contained 92% acetonitrile with 8% water. The top layer was treated again with sorbitol 76 g (20% w/v), mixed and placed in freezer at −18° C. overnight for further separation of water. Sorbitol acted mostly as a dehydrating agent, absorbing most of the water and forming solid lumps. The remaining organic layer was again separated to analyze for its purity. The yield of the top layer was 345 mL (69%) and contained 97% acetonitrile, 2-3% water and 0.26% sorbitol (0.90 g). This layer was distilled at atmospheric pressure and the pure acetonitrile was collected at 81° C. (342 mL, 68.4% yield and contained 98% pure acetonitrile). The sorbitol was recovered by vacuum distillation using a rotary evaporator (40° C., 230 mbar) leaving anhydrous sorbitol in the distillation pot (190 g, 95% recovery).

Example 6: Sorbitol-Induced Extraction of Water from Acetone

To a 1 L glass bottle was added acetone (515 mL), water (300 mL) (36.8% v/v) and the contents were mixed to form a clear colorless solution. A trace amount (ca. 1 mg) of Sudan IV was added to give a pink-red clear solution. Sorbitol was then added in 5-25 g increments until a total of 170 g was obtained (21% wt/v). After addition of each increment, the mixture was agitated until the sorbitol completely dissolved. As the mixture became saturated with sorbitol, the last increment (ca. 10 g) did not completely dissolve. After agitation, the mixture was allowed to settle at room temperature (30 min). Initially, the saturated mixture appeared cloudy and slowly as the solids settled, the mixture formed a less dense top layer of acetone which was red in color due to Sudan IV and a more dense, colorless bottom aqueous layer. The mixture was placed in a freezer at −18° C. overnight resulting in a well-separated top layer (500 mL) and bottom layer (400 mL) wherein the extra volume was caused by the sorbitol. Upon additional storage at −18° C., the sorbitol crystallized out of the aqueous layer. The cold fluid was poured into a separatory funnel and the layers were separated. The yield of the top layer was 450 mL and contained 80% acetone with 20% water. This layer was distilled at reduced pressure (40° C., 550 mbar) using a rotary evaporator (230 mL, 45% yield) and contained 95% pure acetone by IR spectral analysis.

Example 7: Glycerol-Induced Extraction of Water from Hexanes

To 500 mL of hexanes was added 50 mL of water and a trace of indicator Sudan IV. The contents were mixed to yield a slightly pink colored top layer which was spotted with droplets of water and a bottom layer which was clear and colorless. The bottom layer was removed using a separatory funnel. The top layer was treated with 10 g of glycerol and mixed to give a top layer that contained droplets of aqueous glycerol and a bottom layer of aqueous glycerol. The bottom layer was removed. Then the top layer was drained into a clean, dry Erlenmeyer flask leaving behind the droplets of aqueous glycerol on the walls of the separatory funnel. The fluid in the Erlenmeyer flask was decanted into a clean, dry separatory funnel to give a clear pink-red solution with no spotting on the walls. A residual amount (1 mL) of aqueous glycerol was removed. The top layer was drained and distilled under reduced pressure (40° C., 330 mbar) using a rotary evaporator. The first 30 mL of distillate was discarded and 430 mL (86% yield) of greater than 99% water-free hexanes (as indicated by IR spectral analysis which showed the absence of an absorption at 1640 cm$^{-1}$) was obtained.

Example 8: Sorbitol-Induced Extraction of Water from Hexanes

To 500 mL of hexanes was added 50 mL of water and a trace of indicator Sudan IV. The contents were mixed to yield a slightly pink colored top layer which was spotted with droplets of water and a bottom layer which was clear and colorless. The bottom layer was removed using a separatory funnel. The top layer was treated with 1.0 g of sorbitol and mixed to give a liquid bottom layer of aqueous sorbitol and droplets of aqueous sorbitol on the walls of the flask. The top layer was decanted into an Erlenmeyer flask and then decanted a second time leaving droplets of aqueous sorbitol in the original Erlenmeyer flask. The decantant was distilled at atmospheric pressure at 65-68° C. to obtain 450 mL of greater than 99% water-free hexanes (as indicated by IR spectral analysis which showed the absence of an absorption at 1640 cm$^{-1}$).

Example 9: Comparison to Traditional Method: Azeotropic Distillation of Acetonitrile/Water A 1.0 L of a 1:1 mixture of acetonitrile and water was subjected to traditional azeotropic distillation. Two separate distillates were collected where first distillate was collected between 76-81° C. (550 mL) and was analyzed to be 86% pure acetonitrile. The volume of second distillate was collected between 81-99° C. (250 mL) and was analyzed to be only 75% pure acetonitrile. The experiment clearly demonstrated that maximum purity level achieved by distillation was 86% pure acetonitrile.

Example 10: Glycerol-Induced Extraction of Water from a Commercial Formulation of a Non-Acetone Nail Polish Remover To a clear, 12 oz., plastic (PETE) bottle was added 200 mL of non-acetone nail polish remover. The principal ingredients of the formulation were indicated as ethyl acetate, alcohol, water and propylene carbonate. Then 20 mL of glycerol was added and the mixture was shaken which resulted in a cloudy suspension that separated into two layers in 15-30 min at room temperature. The layers were separated by piercing a small hole (<0.1 mm×5 mm) in the base of the bottle with a knife and inverting the bottle such that the liquid laid at the base of the bottle. The cap was loosened and the lower aqueous layer was allowed to drip out (50 mL) through the hole. Once the separation of the aqueous layer was completed, the remaining upper organic phase was poured into a separate bottle for storage (150 mL).

Example 11. Determination of Cloud Point and Effect of Container on Phase Separation To an 8 dram glass vial, 125 mL glass Erlenmeyer flask and 1 L glass bottle was added 10, 100, and 1000 mL of acetonitrile/water (50:50% v/v), respectively. To a 15 mL polypropylene centrifuge tube, 150 mL and 1 L plastic bottle was added 10, 100, and 1000 mL of acetonitrile/water (50:50% v/v), respectively. To an 8 dram glass vial and a 15 mL polypropylene centrifuge tube was added 1.0 g of glass beads (2 mm diameter) and 10 mL of acetonitrile/water (50:50% v/v). To each sample, glycerol was added in aliquots and the solution was mixed to dissolve the glycerol. The amount of glycerol corresponding to a cloudy appearance of the solution was determined to be the cloud point. The results are shown in Table 3.

TABLE 3

Cloud point and effect of container on phase separation.

| entry | Container | Volume (mL, 50:50, v/v ACN$^a$/water) | Amount(g) of Gly$^a$ at cloud point | Relative % change in % Gly at cloud point |
|---|---|---|---|---|
| 1 | Glass/8 dram | 10 | 2.08 | |
| 2$^b$ | Glass/8 dram | 10 | 2.13 | 1.13%$^c$ |
| 3 | Plastic/15 mL | 10 | 2.00 | −4.00% |
| 4$^b$ | Plastic/15 mL | 10 | 2.05 | −1.44% |
| 5 | Glass/125 mL | 100 | 19.5 | −6.25% |
| 6 | Plastic/150 mL | 100 | 19.0 | −9.47% |
| 7 | Glass/1 L | 1000 | 170 | −18.3% |
| 8 | Plastic/1 L | 1000 | 165 | −20.7% |

$^a$ACN is acetonitrile, Gly is glycerol.
$^b$Glass beads (1.0 g, 2 mm dia) added to container.
$^c$Calculation performed relative to entry 1 (% Gly 20.8): (% Gly entry x − 20.8)/20.8. A positive value indicates an increase in % Gly is required to reach cloud point and a negative value indicates a decrease in % Gly is required.

Example 12: Glycerol-Induced Extraction of Water from Diesel Fuel and Extraction of Diesel Fuel from Water To 1.0 L of diesel fuel (obtained from a local gas station) was added 100 mL of water. The contents were mixed and allowed to settle for 1 h to yield a top organic layer and an initial bottom aqueous layer (100 mL, AQ 1). The bottom layer was removed using a separatory funnel. The top layer was treated with 100 g of glycerol and mixed and allowed to settle for 1 h. After the glycerol containing bottom layer (AQ 2) was removed, the upper layer of diesel fuel (950 mL, 95% yield) was analyzed by IR spectroscopy and showed the absence of an absorption at 1640 cm$^{-1}$ which indicated the water was completely removed from the diesel fuel. The initial aqueous layer (AQ 1) was examined by IR spectroscopy which showed absorbances at 1445 and 1380 cm$^{-1}$ characteristic of alkane hydrocarbons present in diesel fuel. Glycerol (20 g, 20%) was added to AQ 1 and upon dissolution of the glycerol, droplets of diesel fuel appeared indicating that the glycerol was extracting the diesel fuel from the water. Analysis of the AQ 1 by IR spectroscopy treated with glycerol indicated a significant reduction (75%) in the hydrocarbon absorbances.

Figure 7A:
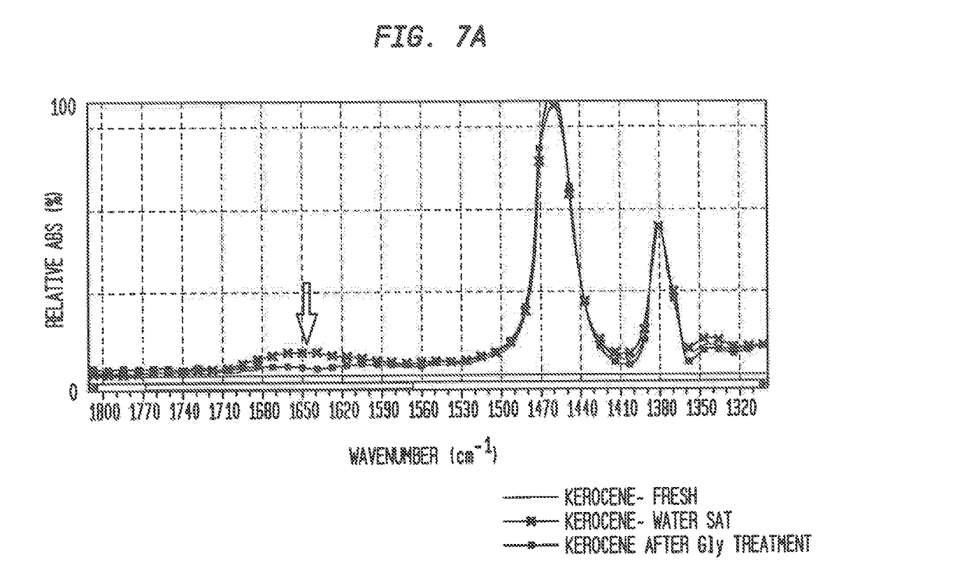
FIG. 7A is a spectral analysis of the glycerol-induced extraction of water from kerosene as described in example 12. The spectrum of fresh kerosene overlays with the spectrum of the glycerol treated kerosene.
Figure 7B:
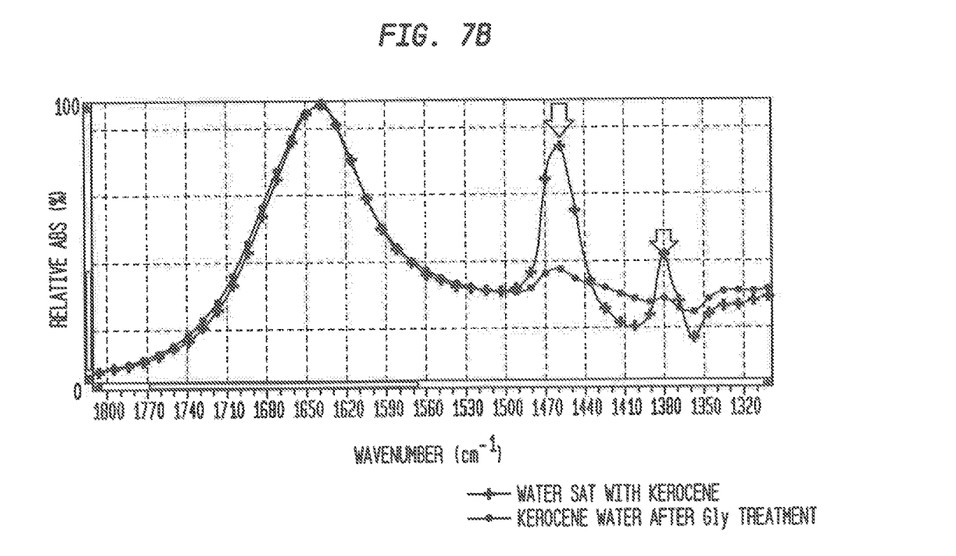
FIG. 7B is a spectral analysis of the glycerol-induced extraction of kerosene from water by addition of glycerol as described in example 12.

Example 13: Glycerol-Induced Extraction of Water from Kerosene and Extraction of Kerosene from Water To 1.0 L of kerosene (obtained from a local hardware store) was added 100 mL of water. The contents were mixed and allowed to settle for 1 h to yield a top organic layer and a bottom aqueous layer (AQ 3). The bottom layer was removed using a separatory funnel. The top layer was treated with 100 g of glycerol and mixed and allowed to settle for 1 h. After the glycerol containing bottom layer (AQ 4) was removed, the upper layer of kerosene (980 mL, 98% yield) was analyzed by IR spectroscopy and showed the absence of an absorption at 1640 cm$^{-1}$ (FIG. 7A) which indicated the water was completely removed from the kerosene. The initial aqueous layer (AQ 3) was examined by IR spectroscopy which showed absorbances at 1445 and 1380 cm$^{-1}$ (FIG. 7B) characteristic of alkane hydrocarbons present in kerosene. Glycerol (20 g, 20%) was added to AQ 3 and upon dissolution of the glycerol, droplets of kerosene appeared indicating that the glycerol was extracting the kerosene from the water. Analysis of the AQ 3 by IR spectroscopy treated with glycerol indicated a significant reduction (80%) in the hydrocarbon absorbances.

Example 14. Quick and Simple PIE Test

To a 50 mL polyethylene centrifuge tube was added 12 mL of a mixture of acetonitrile and water (50/50% v/v) and one "sugar-free" breathmint tablet (1.8 g) containing sorbitol as the major ingredient (i.e., listed first on the ingredient label). The tube was capped and the contents mixed until the tablet dissolved. The contents were allowed to settle for 5 min and separation of the layers was observed as the contents settled to obtain 7.5 mL of a lower aqueous layer and 4.5 mL of an upper organic layer.

REFERENCES

Yesong et al., Enzyme and Microbial Technology, 35:592-597 (2004).
Wang et al., Chemical Engineering Science, 63:2595-2600 (2008).
Dhamole et al., Process Biochemistry, 45:1672-1676 (2010).
Esquijarosa et al., Separation and Purification Technology, 52:95-101 (2006).
J. A. Renard, Journal of Chemical and Engineering Data, 11:169-171 (1966).
Renard et al., Journal of Chemical and Engineering Data, 13:485-488 (1968).
Renard et al., Journal of Chemical and Engineering Data, 10:152-155 (1965).
Renard et al., Journal of Chemical and Engineering Data, 12:33-36 (1967).
Takamuku et al., Journal of Physical Chemistry, 105:6236-6245 (2001).
Maslan et al., Journal of Physical Chemistry, 60(8):1146-1147 (1956).
Wolfson et al., Environ. Chem. Lett., 5:67-71 (2007).
U.S. Patent Application Publication 2011/0108481 A1.

All patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of separating water from an organic liquid from a composition containing water and the organic liquid, comprising adding to the composition a polyol that causes separation of the composition into at least two liquid phases, wherein a first phase is aqueous and the second phase is organic, and wherein the polyol is selected from the group consisting of ethylene glycol, propylene glycol, and glycerol.

2. The method of claim 1, wherein the polyol is glycerol.

3. The method of claim 2, wherein the organic liquid comprises acetonitrile.

4. The method of claim 2, wherein the organic liquid comprises a polar aprotic liquid which is acetonitrile, toluene, ethyl acetate, 2-methyltetrahydrofuran or tetrahydrofuran.

5. The method of claim 2, wherein the organic liquid comprises a polar protic liquid which is 1-butanol, t-butanol, 2-pentanol, isopentyl alcohol, cyclohexanol or 1-octanol.

6. The method of claim 2, wherein the organic liquid comprises a non-polar liquid which is hexane, cyclohexane, kerocene, diesel fuel, biodiesel fuel, a petroleum distillate or gasoline.

7. The method of claim 1, wherein the polyol is ethylene glycol.

8. The method of claim 7, wherein the organic liquid comprises a polar aprotic liquid which is acetonitrile or acetone.

9. The method of claim 7, wherein the organic liquid comprises a nonpolar liquid which is hexane, cyclohexane, kerocene, diesel fuel, biodiesel fuel, a petroleum distillate or gasoline.

10. The method of claim 1, wherein the polyol is propylene glycol.

11. The method of claim 10, wherein the organic liquid comprises a polar aprotic liquid which is acetonitrile or acetone.

12. The method of claim 10, wherein the organic liquid comprises a nonpolar liquid which is hexane, cyclohexane, kerosene, diesel fuel, biodiesel fuel, a petroleum distillate or gasoline.

13. The method of claim 1, wherein the organic liquid that is extracted from the composition has greater than about 80% to about 98% purity.

14. The method of claim 1, wherein the separation of the composition into the two liquid phases is conducted at a temperature from about 25° C. to about −25° C.

15. The method of claim 14, wherein the temperature is from about 25° C. to about −2° C.

16. The method of claim 1, further comprising mechanically separating the aqueous phase from the organic phase.

17. The method of claim 16, wherein the mechanical separation is conducted at room temperature.

18. The method of claim 16, wherein the mechanical separation is conducted at a temperature at or below the freezing point of water, and which temperature is above the freezing point of the organic liquid.

19. The method of claim 1, wherein the adding of the polyol is conducted at room temperature, and the method further comprises lowering the temperature after the polyol is added to the composition.

20. The method of claim 19, wherein the temperature is lowered to about 2° C.

21. The method of claim 19, wherein the temperature is lowered to about −18° C.

22. The method of claim 19, further comprises mechanically separating the aqueous phase from the organic phase at or about the lowered temperature.

23. The method of claim 1, wherein the composition contains about 30% to about 90% of the organic liquid.

* * * * *